| United States Patent [19] | [11] Patent Number: 5,416,236 |
| Kawamura et al. | [45] Date of Patent: May 16, 1995 |

[54] ANILINE DERIVATIVES AND PROCESS FOR PRODUCING THE SAME

[75] Inventors: Yasuo Kawamura; Jun Satow; Kenzou Fukuda; Kaoru Itoh, all of Funabashi; Hiroshi Kita, Chiba, all of Japan

[73] Assignee: Nissan Chemical Industries Ltd., Tokyo, Japan

[21] Appl. No.: 264,761

[22] Filed: Jun. 23, 1994

Related U.S. Application Data

[62] Division of Ser. No. 823,539, Jan. 21, 1992, abandoned.

[30] Foreign Application Priority Data

Jan. 23, 1991 [JP] Japan .................................. 3-006332
Dec. 3, 1991 [JP] Japan .................................. 3-319421

[51] Int. Cl.$^6$ ............................................. C07C 303/08
[52] U.S. Cl. ........................................ 560/13; 564/95; 564/99
[58] Field of Search .................. 564/95, 99; 560/13

[56] References Cited

U.S. PATENT DOCUMENTS

| | | | |
|---|---|---|---|
| 2,414,491 | 1/1947 | Tulagin | 564/95 X |
| 3,734,710 | 5/1973 | Lukaszczyk et al. | 504/333 |
| 3,920,444 | 11/1975 | Harrington et al. | 504/333 |
| 4,349,378 | 9/1982 | Cliff et al. | 564/99 X |
| 4,424,156 | 1/1984 | Hamprecht et al. | 564/99 X |
| 4,483,986 | 11/1984 | Dominianni | 564/99 X |
| 4,507,320 | 3/1985 | DeMarinis et al. | 564/99 |
| 4,629,811 | 12/1986 | Dominianni | 564/99 |
| 4,885,367 | 12/1989 | Yoshikawa et al. | 564/99 X |
| 5,021,333 | 6/1991 | Leyshon et al. | 430/551 |
| 5,084,084 | 1/1992 | Satow et al. | 504/240 |

FOREIGN PATENT DOCUMENTS 0069584  1/1983  European Pat. Off. .

OTHER PUBLICATIONS

*Journal of Agricultural and Food Chemistry,* vol. 22, No. 6, (1974), pp. 1111–1119; Trepka et al, see pp. 1114–1115, Table II, Examples 142, 147, 148.

*Primary Examiner*—José G. Dees
*Assistant Examiner*—Joseph M. Conrad
*Attorney, Agent, or Firm*—Oblon, Spivak, McClelland, Maier & Neustadt

[57] ABSTRACT

Disclosed herein is a process for producing a sulfoneamide represented by the following formula (6) as an intermediate of a 6-haloalkyl-3-phenyluracil derivative, from as a starting material 4-halogeno-3-nitroaniline (9) or 2-halogeno-5-nitroaniline (10):

(wherein X and Y independently represent a halogen atom, R represents a $C_1$–$C_4$ alkyl group or a $C_1$–$C_3$ haloalkyl group and R' represents a $C_1$–$C_4$ alkyl group or a phenyl group).

9 Claims, No Drawings

ANILINE DERIVATIVES AND PROCESS FOR PRODUCING THE SAME

This application is a division of application Ser. No. 07/823,539, filed on Jan. 21, 1992, now abandoned.

BACKGROUND OF THE INVENTION

The present invention relates to a novel intermediate used for producing a 6-haloalkyl-3-phenyluracil derivative [described in Japanese Patent Application Nos. Hei 2-400475 (1990) and Hei 3-314391 (1991)] which is useful as a herbicide and a process for producing the same.

As aniline derivatives, N-(3-amino-4-chlorophenyl)-methanesulfonamide is described in West German Patent Nos 2938633 and 3124172, methyl 5-amino-2-chlorocarbanilate is described in West German Patent No. 2703838, methyl 2-chloro-5-nitrocarbanilate is described in U.S. Pat. No. 2,860,166 and West German Patent Nos. 2703838, 2725146, 2846625 and 2926049, ethyl 5-amino-2-chlorocarbanilate is described in U.S. Pat. No. 3,920,444, ethyl 2-chloro-5-nitrocarbanilate is described in Justus Liebigs Ann. Chem. vol 721. p.14, N-(4-fluoro-3-nitrophenyl)methanesulfonamide is described in U.S. Pat. No. 4,507,479, a methyl ester and a phenyl ester of 2-fluoro-5-nitrocarbanilic acid are discribed in U.S. Pat. No. 4,226,613, and a methyl ester and a phenyl ester of 5-amino-2-fluorocarbanilic acid (since they are not isolated, the physical properties are not described) are described in U.S. Pat. No. 4,227,007.

These literatures only describe these derivatives as an intermediate or a byproduct, and a process for producing these derivatives are not always satisfactory. Provision of a more advantageous process thereof is, therefore, demanded.

In addition, no benzene derivative having both functional groups of carbonate and sulfoneamide and substituted by one or two halogen atom is known at all.

As a result of earnest investigations of a process for producing a 6-haloalkyl-3-phenyluracil derivative [described in Japanese Patent Application Nos. Hei 2-400475 (1990) and Hei 3-314391 (1991)] which is useful as a herbicide, it has been found that an intermediate produced in accordance with the-following scheme is useful as an intermediate for producing the 6-haloalkyl-3-phenyluracil derivative:

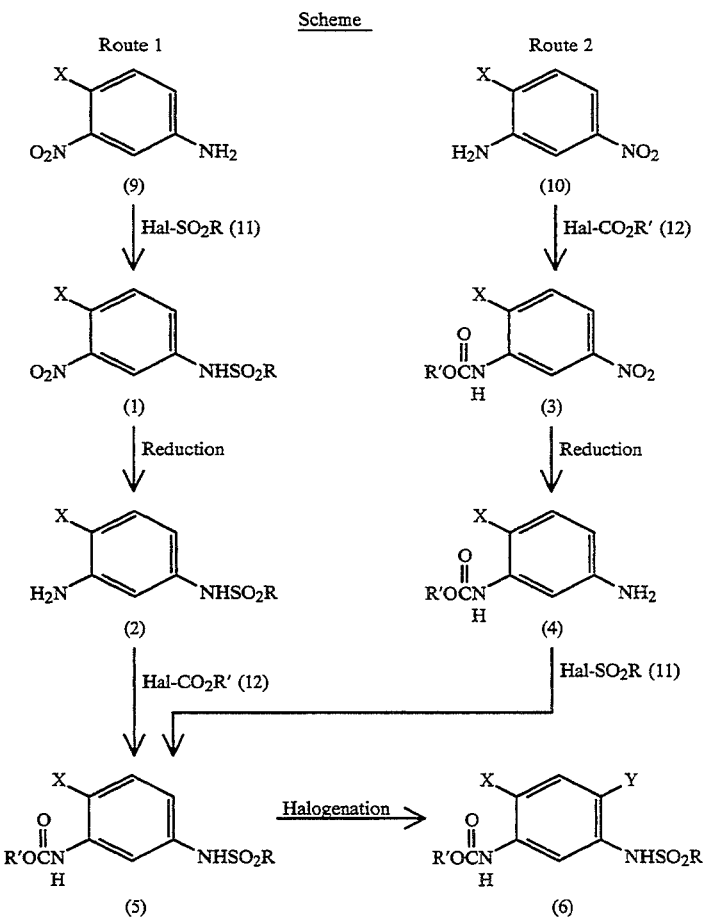

(wherein X, Y and Hal independently represent a halogen atom, R represents a $C_1$–$C_4$ alkyl group or a $C_1$–$C_3$ haloalkyl group, and R' represents a $C_1$–$C_4$ alkyl group or a phenyl group). The present invention has been achieved on the basis of this finding.

SUMMARY OF THE INVENTION

In a first aspect of the present invention, there is provided a process for producing a sulfoneamide derivative represented by the following formula (6):

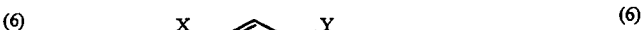

(wherein X and Y independently represent a halogen atom, R represents a $C_1$-$C_4$ alkyl group or a $C_1$-$C_3$ haloalkyl group and R' represents a $C_1$-$C_4$ alkyl group or a phenyl group), comprising the steps of:

reacting 4-halogeno-3-nitroaniline represented by the following general formula (9):

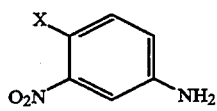

with an alkylsulfonyl halide represented by the following general formula (11):

Hal—$SO_2R$                   (11)

(wherein Hal represents a halogen atom), so as to obtain a nitroaniline derivative represented by the following general formula (1):

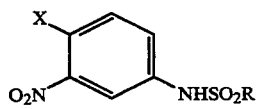

reducing the nitroaniline derivative represented by the formula (1) so as to obtain a diamine derivative represented by the following general formula (2):

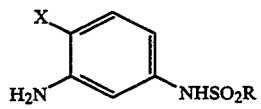

reacting the diamine derivative represented by the formula (2) with a halogenoformate represented by the following general formula (12):

Hal—$CO_2R'$                 (12)

so as to obtain an anilide derivative represented by the following general formula (5):

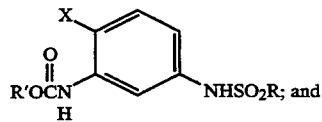

halogenating the anilide derivative represented by the formula (5).

In a second aspect of the present invention, there is provided a process for producing a sulfonamide derivative represented by the following formula (6):

(wherein X and Y independently represent a halogen atom, R represents a $C_1$-$C_4$ alkyl group or a $C_1$-$C_3$ haloalkyl group and R' represents a $C_1$-$C_4$ alkyl group or a phenyl group), comprising the steps of:

reacting 2-halogeno-5-nitroaniline represented by the following general formula (10):

with a halogenoformate represented by the following general formula (12):

Hal—$CO_2R'$                 (12)

(wherein Hal represents a halogen atom)

so as to obtain a nitrocarbanilide derivative represented by the following general formula (3):

reducing the nitrocarbanilide derivative represented by the formula (3) so as to obtain an aminocarbanilide derivative represented by the following general formula (4):

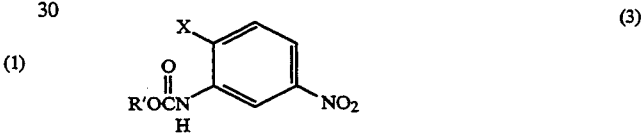

reacting the aminocarbanilide derivative represented by the general formula (4) with an alkylsulfonyl halide represented by the following general formula (11):

Hal—$SO_2R$                 (11)

so as to obtain an anilide derivative represented by the following general formula (5):

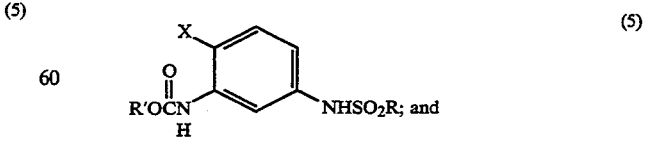

halogenating the anilide derivative represented by the formula (5).

In a third aspect of the present invention, there is provided a process for producing a nitroaniline derivative represented by the following formula (1):

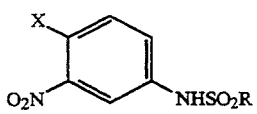  (1)

(wherein X represents a halogen atom and R represents a $C_1$–$C_4$ alkyl group or a $C_1$–$C_3$ haloalkyl group), comprising the step of reacting 4-halogeno-3-nitroaniline represented by the following general formula (9):

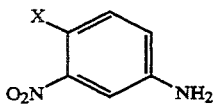  (9)

with an alkylsulfonyl halide represented by the following general formula (11):

Hal—$SO_2R$  (11)

(wherein Hal represents a halogen atom).

In a fourth aspect of the present invention, there is provided a process for producing a diamine derivative represented by the following formula (2):

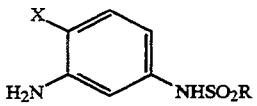  (2)

(wherein X represents a halogen atom and R represents a $C_1$–$C_4$ alkyl group or a $C_1$–$C_3$ haloalkyl group), comprising the step of reducing a nitroaniline derivative represented by the following general formula (1):

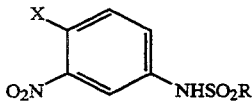  (1)

In a fifth aspect of the present invention, there is provided a process for producing an anilide derivative represented by the following general formula (5):

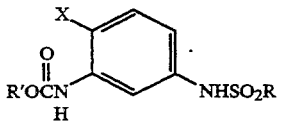  (5)

(wherein X represents a halogen atom, R represents a $C_1$–$C_4$ alkyl group or a $C_1$–$C_3$ haloalkyl group and R' represents a $C_1$–$C_4$ alkyl group or a phenyl group), comprising the step of reacting a diamine derivative represented by the following formula (2):

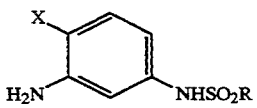  (2)

with a halogenoformate represented by the following general formula (12):

Hal—$CO_2R'$  (12)

(wherein Hal represents a halogen atom).

In a sixth aspect of the present invention, there is provided a process for producing a nitrocarbanilide derivative represented by the following general formula (3):

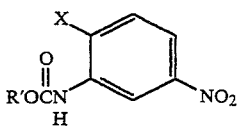  (3)

(wherein X represents a halogen atom and R' represents a $C_1$–$C_4$ alkyl group or a phenyl group) comprising the step of reacting 2-halogeno-5-nitroaniline represented by the following general formula (10):

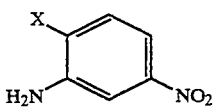  (10)

with a halogenoformate represented by the following general formula (12):

Hal—$CO_2R'$  (12)

(wherein Hal represents a halogen atom).

In a seventh aspect of the present invention, there is provided a process for producing an aminocarbanilide derivative represented by the following general formula (4):

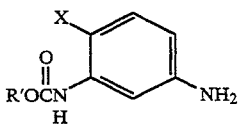  (4)

(wherein X represents a halogen atom and R' represents a $C_1$–$C_4$ alkyl group or a phenyl group) comprising the step of reducing a nitrocarbanilide derivative represented by the following general formula (3):

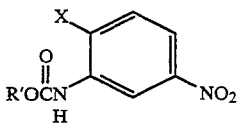  (3)

8. In an eighth aspect of the present invention, there is provided a process for producing an anilide derivative represented by the following general formula (5):

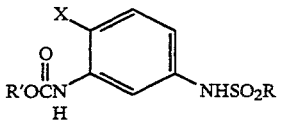  (5)

(wherein X represents a halogen atom, R represents a $C_1$–$C_4$ alkyl group or a $C_1$–$C_3$ haloalkyl group and R' represents a $C_1$–$C_4$ alkyl group or a phenyl group), comprising the step of reacting an aminocarbanilide derivative represented by the following general formula (4):

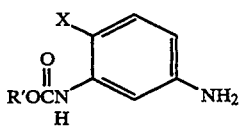
(4)

with an alkylsulfonyl halide represented by the following general formula (11):

Hal—SO₂R (11)

(wherein Hal represents a halogen atom).

In a ninth aspect of the present invention, there is provided a process for producing a sulfonamide derivative represented by the following formula (6):

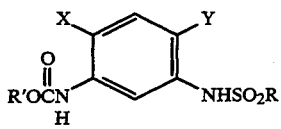
(6)

(wherein X and Y independently represent a halogen atom, R represents a $C_1$-$C_4$ alkyl group or a $C_1$-$C_3$ haloalkyl group and R' represents a $C_1$-$C_4$ alkyl group or a phenyl group), comprising the step of halogenating an anilide derivative represented by the following general formula (5):

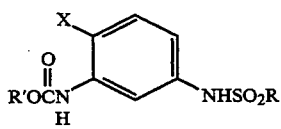
(5)

In a tenth aspect of the present invention, there is provided a nitroaniline derivative are represented by the following general formula (1):

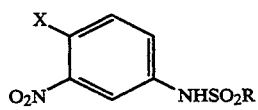
(1)

wherein X represents a halogen atom and R represents a $C_1$-$C_4$ alkyl group or a $C_1$-$C_3$ haloalkyl group, provided that when X is a fluorine atom, R is not a methyl group.

In an eleventh of the present invention, there is provided a diamine derivative represented by the following formula (2):

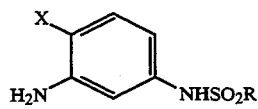
(2)

wherein X represents a halogen atom, R represents a $C_1$-$C_4$ alkyl group or a $C_1$-$C_3$ haloalkyl group, provided that when X is a chlorine atom, R is not a methyl group.

In a twelfth aspect of the present invention there is provided a nitrocarbanilide derivative represented by the following general formula (3):

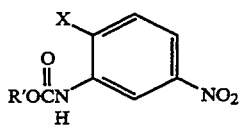
(3)

wherein X represents a halogen atom and R' represents a $C_1$-$C_4$ alkyl group or a phenyl group, provided that when X is a fluorine atom or a chlorine atom, R' is not a methyl group, when X is a fluorine atom, R' is not a phenyl group, and when X is a chlorine atom, R' is not an ethyl group.

In a thirteenth aspect of the present invention there is provided an aminocarbanilide derivative represented by the following general formula (4):

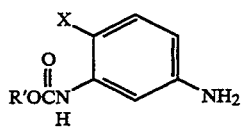
(4)

wherein X represents a halogen atom and R' represents a $C_1$-$C_4$ alkyl group or a phenyl group, provided that when X is a fluorine atom or a chlorine atom, R' is not a methyl group, when X is a fluorine atom, R' is not a phenyl group, and when X is a chlorine atom, R' is not an ethyl group.

In a fourteenth aspect of the present invention, there is provided an anilide derivative represented by the following general formula (5):

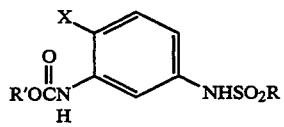
(5)

wherein X represents a halogen atom, R represents a $C_1$-$C_4$ alkyl group or a $C_1$-$C_3$ haloalkyl group and R' represents a $C_1$-$C_4$ alkyl group or a phenyl group.

In a fifteenth aspect of the present invention, there is provided a sulfonamide derivative represented by the following formula (6):

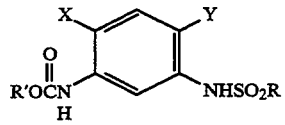
(6)

wherein X and Y independently represent a halogen atom, R represents a $C_1$-$C_4$ alkyl group or a $C_1$-$C_3$ haloalkyl group and R' represents a $C_1$-$C_4$ alkyl group or a phenyl group.

DETAILED DESCRIPTION OF THE INVENTION

In the above-described scheme, route 1 shows the process of producing a compound (5) with a high yield by subjecting a nitroaniline derivative (9) to sulfoneamidation, reducing the thus-obtained sulfoneamide derivative and carbamating the reduced product. Route 2 shows the process of producing a compound (5) with a high yield by carbamating a nitroaniline derivative (10), reducing the carbamated derivative and subjecting the reduced product to sulfoneamidation, and a process of producing a compound (6) with a high yield by halogenating the thus-obtained compound (5) positionally selectively.

These steps may be carried out either sequentially or continuously by appropriately selecting the conditions. A compound (8) can be manufactured from the thus-obtained compound (6) [described in Japanese Patent Application Nos. Hei 2-400475 (1990) and Hei 3-314391 (1991)] by the route in the following route.

Reference scheme

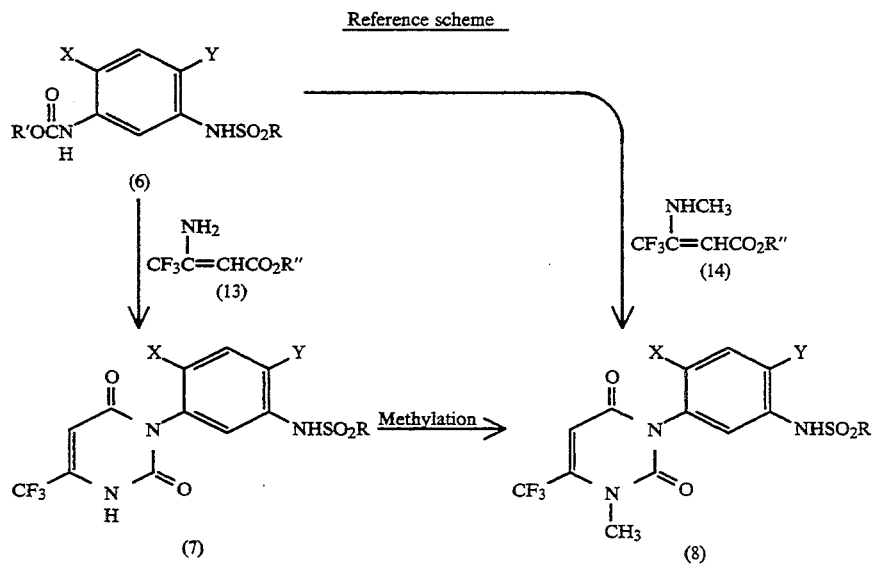

(wherein X, Y, R and R' represents the same as defined above, and R" represents a $C_1$–$C_6$ alkyl group, a phenyl group or a benzyl group).

The respective steps in the scheme will be explained in detail in the following.

(A): Production of a compound (1) from the compound (9)

Ordinarily, the compound (11) of 0.5 to 3.0 mol, preferably 0.8 to 1.5 mol based on the compound (9) is used. A base of 0.5 to 10 mol, preferably 0.8 to 5.0 mol based on the compound (9) is used. The base may be used as a solvent.

As the base, nitrogen-containing organic bases such as pyridine, triethylamine, N,N-dimethylaniline, N,N-diethylaniline, 4-(N,N-dimethylamino)pyridine and 1,4-diazabicyclo[2.2.2]octane, and inorganic bases such as sodium hydroxide, potassium hydroxide, sodium carbonate, potassium carbonate and sodium hydrogencarbonate are usable.

A solvent is ordinarily necessary for the reaction. As the solvent, aliphatic hydrocarbons such as hexane, heptane, ligroin and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutylonitrile; tertiary amines such as pyridine and N,N-diethylaniline; acid amides such as N,N-dimethylacetamide, N,N-dimethylformamide and N-methylpyrrolidone; sulfur-containing compounds such as dimethylsulfoxide and sulfolane; and a mixture thereof may be exemplified. Among these, the aromatic hydrocarbons, halogenareal hydrocarbons, tertiary amines and a mixture thereof are preferable.

The reaction temperature is ordinarily −10° to 180° C., preferably 0° C. to a reflux temperature.

The reaction time is ordinarily 1 to 72 hours, preferably 2 to 48 hours.

(B): Production of a compound (2) from the compound (1)

For reduction, a reagent reduction and catalytic hydrogenation may be adopted.

(Reagent reduction)

Ordinarily, a reducing agent of 1 to 20 mol, preferably 2 to 10 mol based on the compound (1) is used.

As the reducing agent, metals and metal salts such as zinc, aluminum, tin, stannous chloride and iron will be cited.

The reaction ordinarily requires a solvent. As the solvent, organic acids such as formic acid and acetic acid; inorganic acids such as hydrochloric acid, hydrobromic acid and sulfuric acid; esters such as ethyl acetate and butyl acetate; ketones such as acetone and methyl ethyl ketone; ethers such as tetrahydrofuran and dioxane; alcohols such as methanol and ethanol; water; and a mixture thereof may be exemplified.

The reaction temperature is ordinarily 0° to 150° C., preferably 40° C. to a reflux temperature.

The reaction time is ordinarily 15 minutes to 24 hours, preferably 0.5 to 8 hours.

(Catalytic hydrogenation)

Ordinarily, hydrogen of 2.8 to 3.2 mol, preferably 2.9 to 3.1 mol based on the compound (1) is used. A catalyst of 0.001 to 10 wt %, preferably 0.005 to 5 wt % based on the compound (1) is used.

As examples of the catalyst, platinum catalysts such as platinum oxide (IV), platinum black, platinum carbon powder, and platinum carbon sulfide powder; palladium catalysts such as palladium carbon powder, palladium alumina powder, palladium black and palladium oxide; osmium catalysts such as osmium carbon powder; rhenium catalysts such as rhenium carbon powder; and nickel catalysts such as Raney nickel will be cited.

It is possible to add an inorganic acid such as sulfuric acid, hydrochloric acid, phosphoric acid and perchloric acid, and a base such as pyridine and triethylamine in order to accelerate the reaction.

The reaction ordinarily requires a solvent. As the solvent, organic acids such as formic acid and acetic acid; esters such as ethyl acetate and butyl acetate; ethers such as diethyl ether, tetrahydrofuran and dioxane; alcohols such as methanol and ethanol; aliphatic hydrocarbons such as cyclohexane and heptane; aromatic hydrocarbons such as benzene and toluene; acid amides such as N,N-dimethylformamide; water; and a mixture thereof may be exemplified. Among these, the organic acides, ethers, alcohols, aliphatic hydrocarbons, water and a mixture thereof are preferable.

The reaction temperature is ordinarily 0° to 200° C., preferably 25° to 150° C.

The reaction time is ordinarily 0.5 to 24 hours, preferably 1 to 12 hours.

The reaction pressure is ordinarily 0 to 200 atm, preferably 0 to 100 atm (Gauge).

(C) Production of the compound (5) from a compound (2)

Ordinarily, a compound (12) of 0.5 to 2.0 mol, preferably 0.8 to 1.2 mol based on the compound (2) is used.

Ordinarily, a base of 0.5 to 2.0 mol, preferably 0.8 to 1.5 mol based on the compound (2) is used. The base may be used as a solvent.

As the base, nitrogen-containing organic bases such as pyridine, triethylamine, N,N-dimethylaniline, N,N-diethylaniline, 4-(N,N-dimethylamino)pyridine and 1,4-diazabicyclo[2.2.2]octane and inorganic bases such as sodium hydroxide, potassium hydroxide, sodium carbonate, potassium carbonate and sodium hydrogencarbonate are usable.

A solvent is ordinarily necessary for the reaction. As the solvent, aliphatic hydrocarbons such as hexane, heptane, ligroin and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutylonitrile; tertiary amines such as pyridine and N,N-diethylaniline; acid amides such as N,N-dimethylacetamide, N,N-dimethylformamide and N-methylpyrrolidone; sulfur-containing compounds such as dimethylsulfoxide and sulfolane; and a mixture thereof may be exemplified. Among these, the aromatic hydrocarbons, halogenated hydrocarbons, ketones, nitriles, tertiary amines and a mixture thereof are preferable.

The reaction tempuratrure is ordinarily −10° C. to a reflux temperature.

The reaction time is ordinarily 0.5 to 72 hours, preferably 1 to 12 hours.

(D) Production of a compound (3) from a compound (10)

Ordinarily, a compound (12) of 0.5 to 2.0 mol, preferably 0.8 to 1.5 mol based on the compound (10) is used.

Ordinarily, a base of 0.5 to 2.0 mol, preferably 0.8 to 1.6 mol based on the compound (10) is used. The base may be used as a solvent.

As the base, nitrogen-containing organic bases such as pyridine, triethylamine, N,N-dimethylaniline, N,N-diethylaniline, 4-(N,N-dimethylamino)pyridine and 1,4-diazabicyclo[2.2.2]octane and inorganic bases such as sodium hydroxide, potassium hydroxide, sodium carbonate, potassium carbonate and sodium hydrogencarbonate are usable.

A solvent is ordinarily necessary for the reaction. As the solvent, aliphatic hydrocarbons such as hexane, heptane, ligroin and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutylonitrile; tertiary amines such as pyridine and N,N-diethylaniline; acid amides such as N,N-dimethylacetamide, N,N-dimethylformamide and N-methylpyrrolidone; sulfur-containing compounds such as dimethylsulfoxide and sulfolane; and a mixture thereof may be exemplified. Among these, the aromatic hydrocarbons, halogenated hydrocarbons, ketones, nitriles, tertiary amines and a mixture thereof are preferable.

The reaction temperature is ordinarily −10° C. to a reflux temperature.

The reaction time is ordinarily 0.5 to 72 hours, preferably 1 to 48 hours.

(E) Production of a compound (4) from the compound (3)

The reaction is carried out under the same conditions as those in (B): Production of a compound (2) from the compound (1).

(F) Production of the compound (5) from the compound (4)

Ordinarily, a compound (11) of 0.5 to 3.0 mol, preferably 0.8 to 1.5 mol based on the compound (4) is used.

Ordinarily, a base of 0.5 to 10 mol, preferably 0.8 to 5.0 mol based on the compound (4) is used. The base may be used as a solvent.

As the base, nitrogen-containing organic bases such as pyridine, triethylamine, N,N-dimethylaniline, N,N-diethylaniline, 4-(N,N-dimethylamino)pyridine and 1,4-diazabicyclo[2.2.2]octane, and inorganic bases such as sodium hydroxide, potassium hydroxide, sodium carbonate, potassium carbonate and sodium hydrogencarbonate are usable.

A solvent is ordinarily necessary for the reaction. As the solvent, aliphatic hydrocarbons such as hexane, heptane, ligroin and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutylonitrile; tertiary amines such as pyridine and N,N-diethylaniline; acid amides such as N,N-dimethylacetamide, N,N-dimethylformamide and N-methylpyrrolidone; sulfur-containing compounds such as dimethylsulfoxide and sulfolane; and a mixture thereof may be exemplified. Among these, the aromatic hydrocarbons, halogenated hydrocarbons, tertiary amines and a mixture thereof are preferable.

The reaction temperature is ordinarily −10° to 180° C., preferably 0° C. to a reflux temperature.

The reaction time is ordinarily 1 to 72 hours, preferably 2 to 48 hours.

(G): Production of the compound (6) from the compound (5)

Ordinarily, a halogenating agent of 0.5 to 5.0 mol, preferably 0.8 to 1.5 mol based on the compound (5) is used.

As the halogenating agent, halogens such as chlorine and bromine, hydrogen chloride, sulfuryl chloride, N- chlorosuccineimide, N-bromosuccineimide, N-chloroisocyanuric acid, cuprous bromide and antimony pentachloride are usable.

A solvent is ordinarily necessary for the reaction. As the solvent, organic acids such as formic acid and acetic acid; aliphatic hydrocarbons such as hexane, heptane, ligroin and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; sulfolane; water; and a mixture thereof may be exemplified. Among these, the organic acids, ethers, water and a mixture thereof are preferable.

The reaction temperature is ordinarily 0° to 200° C., preferably 10° to 130° C.

The reaction time is ordinarily 0.5 to 24 hours, preferably 1 to 12 hours.

The thus-obtained sulfoneamide derivative (6) is used as an intermediate for producing a 6-haloalkyl-3-phenyluracil derivative which is useful as a herbicide, as is seen from the later-described reference examples.

The diamine derivative (2), the nitrocarbalinide derivative (3), the aminocarbanilide derivative (4) and the anilide derivative (5) are also useful for an intermediate for producing the sulfoneamide derivative (6).

[EXAMPLES]

Intermediates and a process for producing the same according to the present invention will be explained in more detail with reference to the following examples and a process for producing a herbicide by using the intermediate of the present invention will be explained with reference to the following reference examples. It is to be understood, however, that the present invention is not restricted thereto.

Example 1

Synthesis of
N-(4-fluoro-3-nitrophenyl)ethanesulfonamide

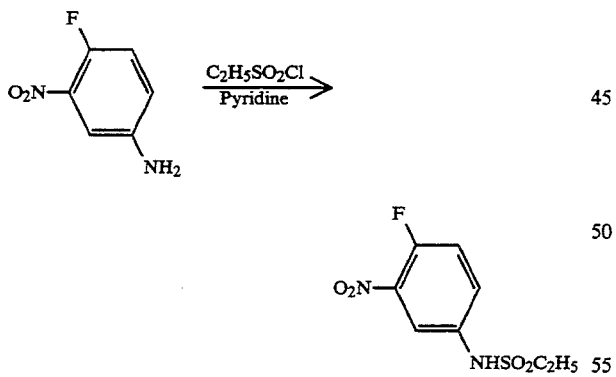

20.2 g (0.129 mol) of 4-fluoro-3-nitroaniline was dissolved in 120 ml of pyridine, and 17.8 g (0.136 mol) of ethanesulfonyl chloride was added dropwise to the solution at a temperature of not higher than 5° C. Thereafter the temperature was raised to room temperature and the reaction was continued for one night. After the pyridine was distilled off, the thus-obtained product was dissolved in ethyl acetate and washed with diluted hydrochloric acid twice, then with water, and with saturated saline solution. The solution was dried over anhydrous sodium sulfate, and the ethyl acetate was distilled off to obtain the crude product (crystals). The crude product was washed with diisopropyl ether, thereby obtaining 29.7 g of the objective product (yield: 93%) in the form of brown crystals. Melting point: 133° to 136° C.

$^1$H-NMR (d$_6$-DMSO): δ1.36 (3H, t, J=7 Hz), 3.16 (2H, q, J =7 Hz), 7.31 (1H, dd, J=10 Hz), 7.63 (1H, ddd, J=2, 7, 10 Hz), 8.07 (1H, dd, J=2, 7 Hz), 10.66 (1H, br s)

Example 2

Synthesis of
N-(3-amino-4-fluorophenyl)ethanesulfonamide

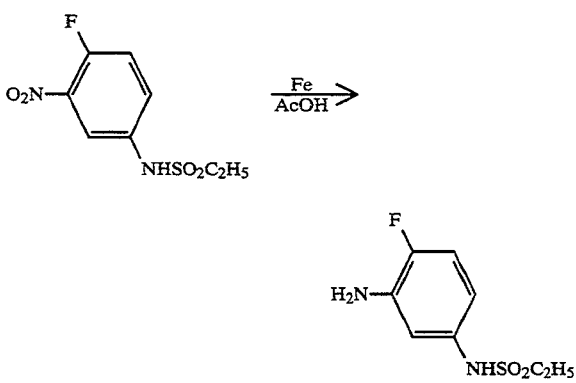

A mixture of 63.1 g (1.13 mol) of iron powder and 120 ml of an aqueous solution of 5% acetic acid was heated to 80° C., and a mixed solution of 28.0 g (0.113 mol) of N-(4-fluoro-3-nitrophenyl)ethanesulfonamide, 116 ml of acetic acid and 116 ml of ethyl acetate was slowly added dropwise to the resultant mixture. After the reaction was continued for 3 hours, the insolubles were filtered out and washed with ethyl acetate. Thereafter the filtrate was distilled to remove the solvent, and the product was dissolved in ethyl acetate and washed with saturated sodium hydrogencarbonate, water and saturated saline solution. The solution was dried over anhydrous sodium sulfate, and the ethyl acetate was distilled off to obtain the crude product (crystals). The crude product was washed with diisopropyl ether, thereby obtaining 22.0 g of the objective product (yield: 89%) in the form of light yellow crystals.

Melting point: 106° to 108° C.

$^1$H-NMR (d$_6$-DMSO): δ1.28 (3H, t, J=7 Hz), 3.05 (2H, q, J=7 Hz), 4.40 (2H, br s), 6.48 (1H, ddd, J=2, 7, 10 Hz), 6.77 (1H, dd, J=2, 7 Hz), 6.89 (1H, dd, J=10 Hz)

Example 3

Synthesis of ethyl
5-ethylsulfonylamino-2-fluorocarbonilate (Process a)

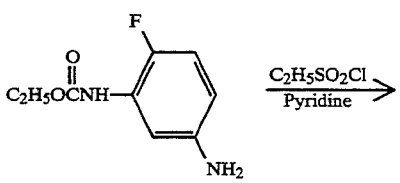

-continued

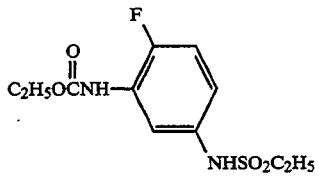

10.0 g (50.5 mmol) of ethyl 5-amino-2-fluorcarbanilate was dissolved in 60 ml of pyridine, and 6.82 g (53.0 mmol) of ethanesulfonyl chloride was added dropwise to the solution at a temperature of not higher than 5° C. Thereafter the temperature was raised to room temperature and the reaction was continued for one night. After the pyridine was distilled off, the thus-obtained product was dissolved in ethyl acetate and washed with diluted hydrochloric acid twice, then with water, and with saturated saline solution. The solution was dried over anhydrous sodium sulfate, and the ethyl acetate was distilled off to obtain the crude product (crystals). The crude product was recrystallized from ethyl acetate-diisopropyl ether, thereby obtaining 9.74 g of the objective product (yield: 67%) in the form of white crystals.

(Process b)

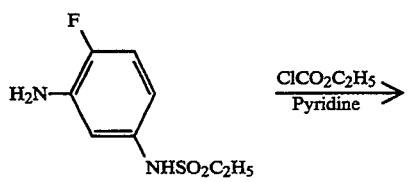

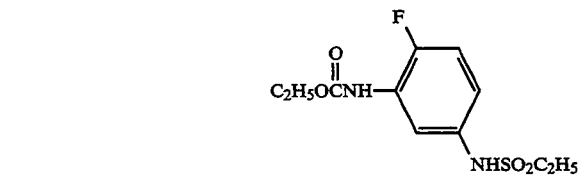

10.7 g (98.2 mmol) of ethyl chloroformate was added dropwise to a mixture of 21.4 g (98.2 mmol) of N-(3-amino-4-fluorophenyl)ethanesulfonamide, 7.76 g (98.2 mmol) of pyridine and 214 ml of dichloromethane at a temperature of not higher than 5° C. Thereafter the temperature was raised to room temperature and the reaction was continued for 5 hours. After the dichloromethane layer was separated out by adding water to the reaction mixture, the dichloromethane layer was washed with saturated saline solution and dried over anhydrous sodium sulfate. Thereafter the dichloromethane was distilled off to obtain the crude product (crystals). The crude product was washed with diisopropyl ether, thereby obtaining 28.0 g of the objective product (yield: 98%) in the form of white crystals. Melting point: 107° to 110° C.

$^1$H-NMR (d$_6$-DMSO): δ 1.30 (6H, t, J=7 Hz), 3.06 (2H, q, J=7 Hz), 4.22 (1H, q, J=7 Hz), 7.00 (2H, br d, J=8 Hz), 7.94 (1H, br d, J=7 Hz), 8.19 (1H, br s), 10.41 (1H, br s)

Example 4

Synthesis of ethyl 2-fluoro-5-nitrocarbanilate

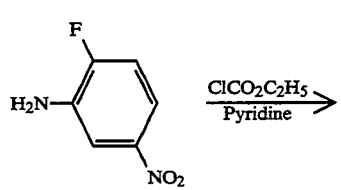

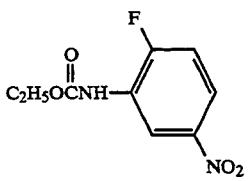

10.7 g (98.9 mmol) of ethyl chloroformate was added dropwise to a mixture of 15.0 g (94.2 mmol) of 2-fluoro-5-nitroaniline, 8.20 g (104 mmol) of pyridine and 150 ml of dichloromethane at a temperature of not higher than 5° C. Thereafter the temperature was raised to room temperature and the reaction was continued for one night. After the dichloromethane layer was separated out by adding water to the reaction mixture, the dichloromethane layer was washed with saturated saline solution and dried over anhydrous sodium sulfate. Thereafter the dichloromethane was distilled off to obtain the crude product (crystals). The crude product was washed with hexane, thereby obtaining 21.1 g of the objective product (yield: 98%) in the form of ocher crystals.

Melting point: 90° to 92° C.

$^1$H-NMR (CDCl$_3$): δ 1.34 (3H, t, J=7 Hz), 4.30 (2H, q, J=7 Hz), 7.22 (1H, br, s), 7.22 (1H, t, J=9 Hz), 7.91 (1H, ddd, J=3, 6, 9 Hz), 9.03 (1H, dd, J=3, 6 Hz)

Example 5

Synthesis of ethyl 5-amino-2-fluorocarbanilate

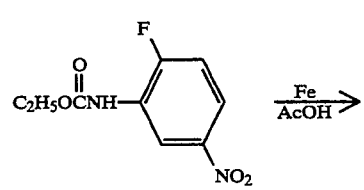

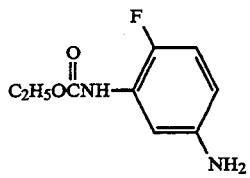

A mixture of 39.4 g (706 mmol) of iron powder and 75 ml of an aqueous solution of 5% acetic acid was heated to 80° C., and a mixed solution of 16.1 g (70.6 mmol) of ethyl 2-fluoro-5-nitrocarbanilate, 72 ml of acetic acid and 72 ml of ethyl acetate was slowly added dropwise to the mixture. After the reaction was continued for 3 hours, the insolubles were filtered out and washed with ethyl acetate. Thereafter the filtrate was distilled to remove the solvent, and the resultant product was dissolved in ethyl acetate and washed with saturated sodium hydrogencarbonate, water and saturated saline solution. The solution was dried over anhydrous sodium sulfate, and the ethyl acetate was distilled off to obtain the crude product (crystals). The crude product was washed with diisopropyl ether, thereby obtaining 12.8 g of the objective product (yield: 91%) in the form of light yellow crystals.

Melting point: 88° to 89° C.

$^1$H-NMR (CDCl$_3$): δ1.24 (3H, t, J=7 Hz), 3.78 (2H, br s), 4.19 (2H, q, J=7 Hz), 6.23 (1H, ddd, J=2, 7, 10 Hz), 6.80 (1H, dd, J=10 Hz), 7.23 (1H, br s), 7.44 (1H, dd, J=2, 7 Hz)

Example 6

Synthesis of ethyl 4-chloro-5-ethylsulfonylamino-2-fluorocabanilate (Process a)

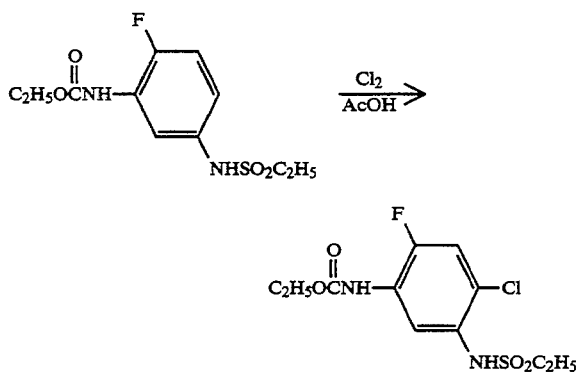

1.00 g (3.45 mmol) of ethyl 5-ethylsulfonylamino-2-fluorocarbanilate was dissolved in 10 ml of acetic acid, and chlorine gas was added to the resultant solution at a temperature of not higher than 25° C. until the starting material disappeared. After the reaction was completed, the surplus chlorine gas was removed by blowing nitrogen gas thereinto, and diisopropyl ether was added. The precipitated crystals were filtered out to obtain 0.76 g of the objective product (yield: 68%) in the form of white crystals.

(Process b)

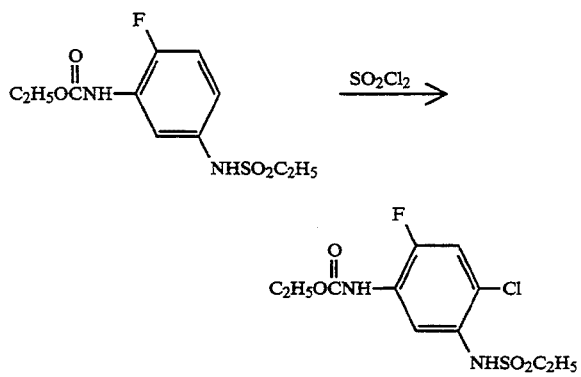

0.50 g (1.72 mmol) of ethyl 5-ethylsulfonylamino-2-fluorocarbanilate was added to 4 ml of sulfuryl chloride. The sulfuryl chloride was distilled off after 10 minutes, and the resultant product was dissolved in ethyl acetate. The solution was washed with water and a saturated saline solution, and dried over anhydrous sodium sulfate. The ethyl acetate was distilled off to obtain the crude product. The crude product was washed with diisopropyl ether, thereby obtaining 0.21 g of the objective product (yield: 38%) in the form of white crystals.

(Process c)

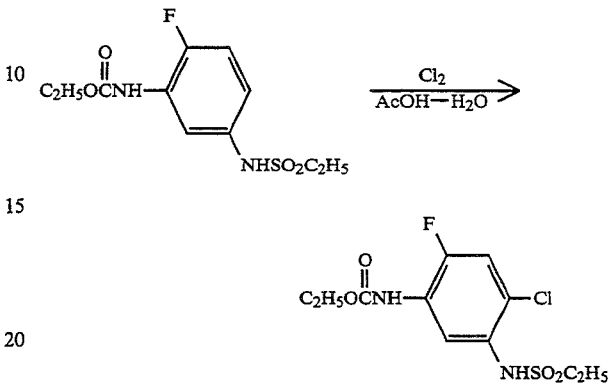

0.50 g (1.72 mmol) of ethyl 5-ethylsulfonylamino-2-fluorocarbanilate was dissolved in a mixed solution of 12 ml of acetic acid and 1 ml of water, and chlorine gas was added to the resultant solution at a temperature of not higher than 25° C. until the starting material disappeared. After the reaction was completed, the surplus chlorine gas was removed by blowing nitrogen gas thereinto, and water was added. The precipitated crystals were filtered out and dried to obtain 0.49 g of the objective product (yield: 88%) in the form of white crystals.

Melting point: 162° to 164° C.

$^1$H-NMR (d$_6$-DMSO): δ1.28 (3H, t, J=7 Hz), 1.32 (3H, t, J=7 Hz), 3.08 (2H, q, J=7 Hz), 4.12 (2H, q, J=7 Hz), 7.13 (1H, d, J=9 Hz), 7.88 (1H, d, J=7 Hz), 8.88 (1H, br s), 8.94 (1H, br s)

Example 7

Synthesis of N-(3-amino-4-fluorophenyl)ethanesulfonamide

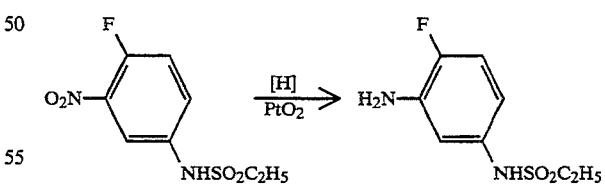

50.4 mg (5 wt %) of platinum oxide (Adams catalyst) was added to a mixture of 1.00 g (4.03 mmol) of N-(4-fluoro-3-nitrophenyl)ethanesulfoneamide and 40 ml of ethanol, and the resultant mixture was stirred until 285 ml of hydrogen was absorbed. The reaction mixture was filtered through a glass filter to remove the catalyst, and the solvent was then distilled off under a reduced pressure. Thus, 850 mg of the objective product (yield: 97%) was obtained in the form of light brown crystals.

Example 8

Synthesis of methyl 5-ethylsulfonylamino-2-fluorocarbanilate

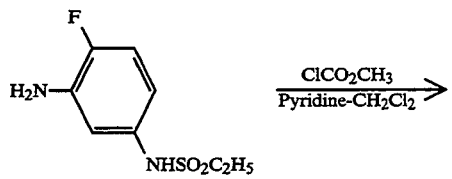

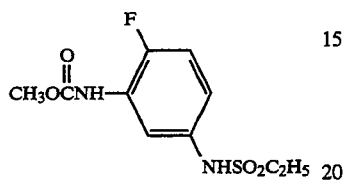

22.1 g (229 mmol) of methyl chloroformate was added dropwise to a mixture of 50.0 g (229 mmol) of N-(3-amino-4-fluorophenyl)ethanesulfonamide, 18.1 g (229 mmol) of pyridine and 500 ml of dichloromethane at a temperature of not higher than 5° C. Thereafter the temperature was raised to room temperature and the reaction was continued for 5 hours. After the dichloromethane layer was separated out by adding water to the resultant mixture, the dichloromethane layer was washed with saturated saline solution and dried over anhydrous sodium sulfate. Thereafter the dichloromethane was distilled off to obtain the crude product (crystals). The crude product was washed with diisopropyl ether, thereby obtaining 61.0 g of the objective product (yield: 96%) in the form of light brown crystals.

Example 9

Synthesis of ethyl 5-amino-2-fluorocarbanilate

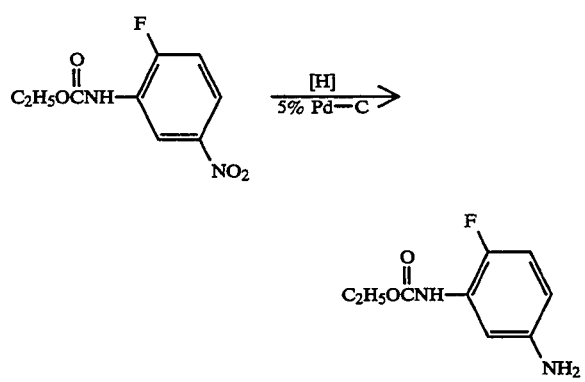

100.3 mg (10 wt %) of 5% palladium carbon (containing water) was added to a mixture of 1.00 g (4.39 mmol) of ethyl 2-fluoro-5-nitrocarbanilate and 20 ml of ethanol, and the resultant mixture was stirred until 309 ml of hydrogen was absorbed. The reaction mixture was filtered to remove the catalyst, and the solvent was then distilled off under a reduced pressure. Thus, 700 mg of the objective product (yield: 81%) was obtained in the form of light brown crystals.

Example 10

Synthesis of ethyl 5-methylsulfonylamino-2-fluorocarbanilate

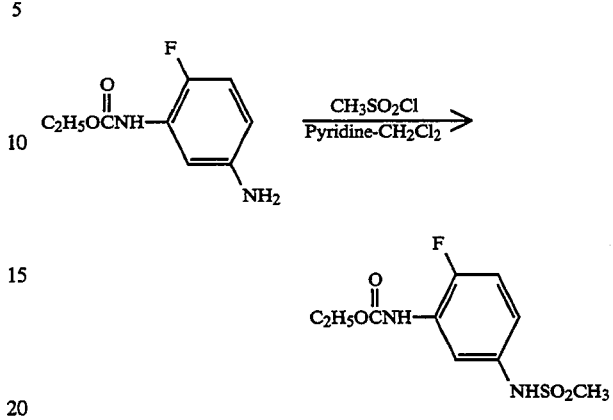

61.1 g (533 mmol) of methanesulfonyl chloride was added dropwise to a mixture of 96.0 g (485 mmol) of ethyl 5-amino-2-fluorocarbanilate, 46.0 g (582 mmol) of pyridine and 700 ml of dichloromethane at a temperature of not higher than 5° C. Thereafter the temperature was raised to room temperature and the reaction was continued for one night. After the solvent was distilled off, the resultant product was dissolved in ethyl acetate and washed with diluted hydrochloric acid twice, then with water, and with saturated saline solution. The resultant solution was dried over anhydrous sodium sulfate, and the ethyl acetate was distilled off to obtain the crude procut (crystals). The crude product was washed with diisopropyl ether, thereby obtaining 126 g of the objective product (yield: 94%) in the form of light brown crystals.

Example 11

Synthesis of ethyl 4-chloro-5-ethylsulfonylamino-2-fluorocarbanilate

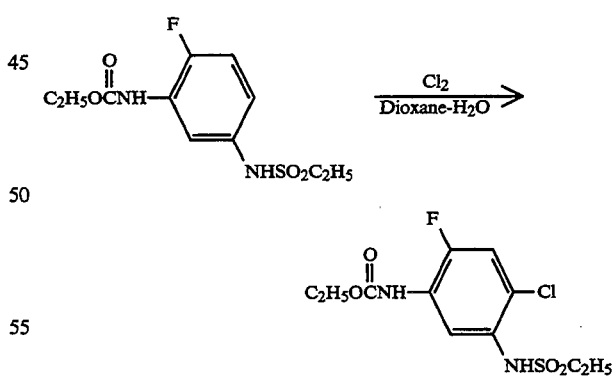

0.50 g (1.72 mmol) of ethyl 5-ethylsulfonylamino-2-fluorocarbanilate was dissolved in a mixture of 5 ml of dioxane and 1 ml of water, and chlorine gas was added to the resultant solution at a temperature of not higher than 25° C. until the starting material disappeared. After the reaction was completed, the surplus chlorine gas was removed by blowing nitrogen gas thereinto, and water was added. The precipitates crystals were filtered out and dried to obtain 0.48 g of the objective product (yield: 86%) in the form of light brown crystals.

Example 12

Synthesis of ethyl 4-chloro-5-methylsulfonylamino-2-fluorocarbanilate

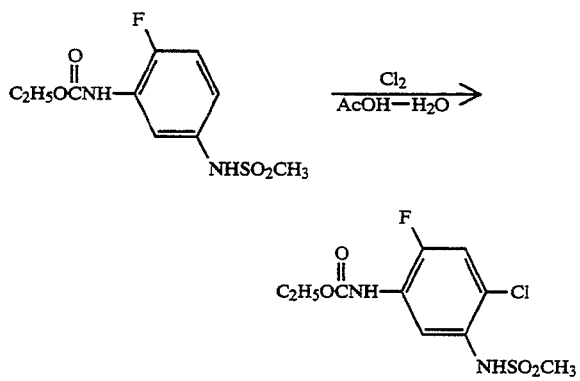

80.6 g (292 mmol) of ethyl 5-methylsulfonylamino-2-fluorocarbanilate was dissolved in a mixture of 1075 ml of acetic acid and 100 ml of water, and chlorine gas was added to the resultant solution at a temperature of not higher than 25° C. until the starting material disappeared. After the reaction was completed, the surplus chlorine gas was removed by blowing nitrogen gas thereinto, and hexane was added. The precipitates crystals were filtered out to obtain 81.4 g of the objective product (yield: 90%) in the form of yellow crystals.

Reference Example 1

Synthesis of 3-(4-chloro-5-ethylsulfonylamino-2-fluorophenyl)-6-trifluoromethyl-2,4(1H,3H)-pyrimidinedione

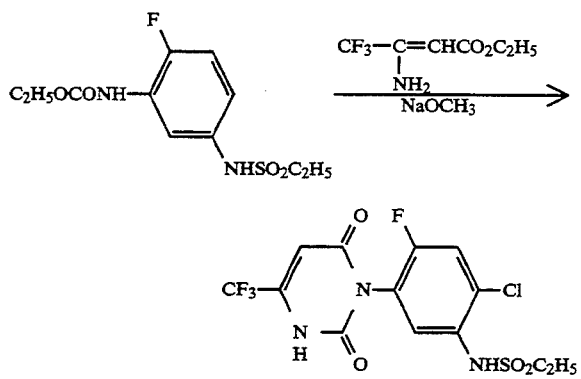

1.06 g (5.77 mmol) of ethyl 3-amino-4,4,4-trifluorocrotonate was dissolved in 6.2 ml of N,N-dimethylformamide and 0.82 g (14.4 mmol) of sodium methoxide was added thereto. The reaction mixture was cooled to not higher than 5° C. after 10 minutes, and 1.56 g (4.81 mmol) of ethyl 4-chloro-5-ethylsulfonylamino-2-fluorocarbanilate was added thereto. The resultant mixture was heated to 110° C. and reacted for 4 hours. After the reaction was completed, N,N-dimethylformamide was distilled off and the resultant product was dissolved in water. The thus-obtained solution was washed with diethyl ether 3 times and thereafter concentrated hydrochloric acid was added thereto to pH 2. The precipitated crystals were filtered out, washed with water and dried to obtain 1.54 g of the objective product (yield: 77%) in the form of light yellow crystals.

Melting point: 190° to 192° C.

$^1$H-NMR (d$_6$-DMSO): δ1.36 (3H, t, J=7 Hz), 3.12 (2H, q, J=7 Hz), 6.19 (1H, s), 7.44 (1H, d, J=9 Hz), 7.58 (1H, d, J=7 Hz), 8.86 (1H, br s), 9.20 (1H, br s)

Reference Example 2

Synthesis of 3-(4-chloro-5-ethylsulfonylamino-2-fluorophenyl)-1-methyl-6-trifluoromethyl-2,4(1H,3H)-pyrimidinedione

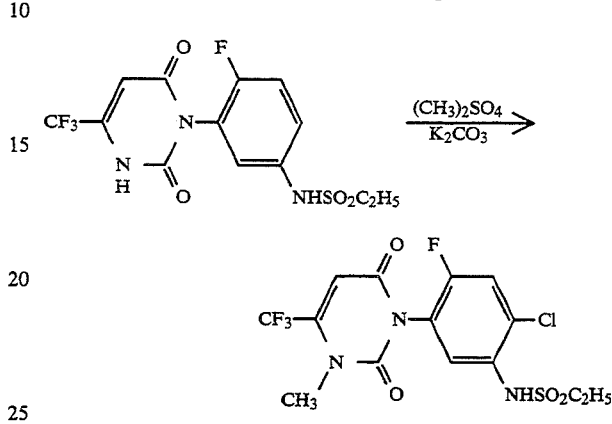

1.00 g (2.41 mmol) of 3-(4-chloro-5-ethylsulfonylamino-2-fluorophenyl)-6-trifluoromethyl-2,4(1H,3H)-pyrimidinedione was dissolved in 10 ml of acetone, and 0.17 g (1.20 mmol) of anhydrous potassium carbonate and 0.23 ml (2.41 mmol) of dimethyl sulfate were added thereto and the reaction was continued for 1.5 hours. After acetone was distilled off, the reaction product was dissolved in ethyl acetate, washed with water and saturated saline solution, and dried over anhydrous sodium sulfate. Thereafter the ethyl acetate was distilled off to obtain a crude product. The crude product was recrystallized from chloroformdiethyl ether, thereby obtaining 0.61 g of the objective product (yield: 59%) in the form of light yellow crystals.

Melting point: 176° to 177° C.

$^1$H-NMR (d$_6$-DMSO): δ1.32 (3H, t, J=7 Hz), 3.06 (2H, q, J=7 Hz), 3.43 (3H, s), 6.23 (1H, s), 7.29 (1H, d, J=9 Hz), 7.41 (1H, d, J=7 Hz), 9.11 (1H, br s)

Reference Example 3

Test of herbicidal effect of soil treatment 50 parts of 3-(4-chloro-5-ethylsulfonylamino-2-fluorophenyl)-1-methyl-6-trifluoromethyl-2,4-(1H,3H)pyrimidinedione, 47 parts of Zeeklite (Kaolin clay, produced by Zeeklite Mining Industries Co., Ltd.), 2 parts of Sorpol 5039 (anionic surfactant, produced by Toho Chemical Ind. Co., Ltd.) and 1 part of Carplex (white carbon, produced by Shionogi Co., Ltd.) were uniformly mixed and pulverized to produce a wettable powder.

Sterilized diluvial soil was placed into a plastic box [15 cm(long)×22 cm(wide)×6 cm(deep)], and sowed at random with the seeds of Echinochloa crus-qalli, Digitaria adscendens, Cyperus microiria, Solanum nigrum, Galinsoga ciliata, Rorippa indica, rice, corn, wheat, soybean and cotton. The diluvial soil was then covered with soil to a depth of about 1 cm, and the wettable powder diluted with water was uniformly sprayed onto the surface of the soil at a predetermined rate. The herbicidal effect on the respective grasses was examined after 3 weeks in accordance with the following evaluation criteria:

Standard ratings:
5: Growth control rate of more than 90% (almost completely withered)
4: Growth control rate of from 70 to 90%
3: Growth control rate of from 40 to 70%
2: Growth control rate of from 20 to 40%
1: Growth control rate of from 5 to 20%
0: Growth control rate of less than 5% (almost non-effective)

The above growth control rates were calculated by the following equation:

Growth control rate (%) = (1 − T/N) × 100 where
T: weight of the weed growth above the soil surface of the treated area,
N: weight of the weed grown above the soil surface of the non-treated area.

In Table 1, the respective symbols represent the following grasses.

N (*Echinochloa crus-qalli*), M (*Digitaria adscendens*), K (*Cyperus microiria*), H (*Solanum nilrum*), D (*Galinsoga ciliata*), I (*Rorippa indica*), R (rice), T (corn), W (wheat), S (soybean) and C (cotton)

TABLE 1

| Dosage (g/ha) | N | M | K | H | D | I | R | T | W | S | C |
|---|---|---|---|---|---|---|---|---|---|---|---|
| 10 | 5 | 3 | 5 | 5 | 5 | 5 | 0 | 0 | 0 | 0 | 2 |
| 20 | 5 | 4 | 5 | 5 | 5 | 5 | 1 | 0 | 0 | 0 | 4 |
| 40 | 5 | 5 | 5 | 5 | 5 | 5 | 3 | 0 | 0 | 0 | 5 |

What is claimed is:

1. A process for producing a sulfonamide derivative represented by the following formula (6):

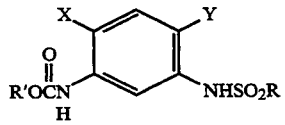
(6)

(wherein X and Y independently represent a halogen atom, R represents a $C_1$–$C_4$ alkyl group or a $C_1$–$C_3$ haloalkyl group and R' represents a $C_1$–$C_4$ alkyl group or a phenyl group), comprising the steps of:
reacting 4-halogeno-3-nitroaniline represented by the following general formula (9):

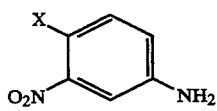
(9)

with an alkylsulfonyl halide represented by the following general formula (11):

  Hal—$SO_2R$ (11)

(wherein Hal represents a halogen atom)so as to obtain a nitroaniline derivative represented by the following general formula (1):

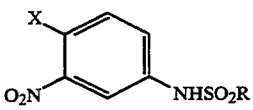
(1)

reducing the nitroaniline derivative represented by the formula (1) so as to obtain a diamine derivative represented by the following general formula (2):

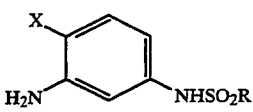
(2)

reacting the diamine derivative represented by the formula (2) with a halogenoformate represented by the following general formula (12):

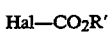  Hal—$CO_2R'$ (12)

so as to obtain an anilide derivative represented by the following general formula (5):

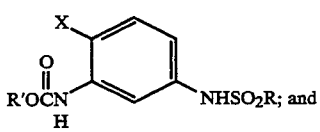
(5)

halogenating the anilide derivative represented by the formula (5).

2. A process for producing a sulfonamide derivative represented by the following formula (6):

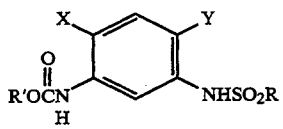
(6)

(wherein X and Y independently represent a halogen atom, R represents a $C_1$–$C_4$ alkyl group or a $C_1$–$C_3$ haloalkyl group and R' represents a $C_1$–$C_4$ alkyl group or a phenyl group), comprising the steps of:
reacting 2-halogeno-5-nitroaniline represented by the following general formula (10):

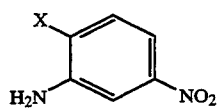
(10)

with a halogenoformate represented by the following general formula (12):

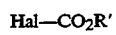  Hal—$CO_2R'$ (12)

(wherein Hal represents a halogen atom)so as to obtain a nitrocarbanilide derivative represented by the following general formula (3):

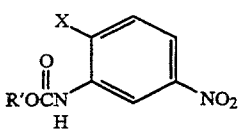
(3)

reducing the nitrocarbanilide derivative represented by the formula (3) so as to obtain an aminocarbanilide derivative represented by the following general formula (4):

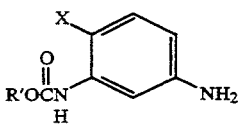
(4)

reacting the aminocarbanilide derivative represented by the general formula (4) with an alkylsulfonyl halide represented by the following general formula (11):

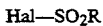
Hal—SO$_2$R (11)

so as to obtain an anilide derivative represented by the following general formula (5):

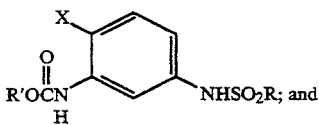
(5)

halogenating the anilide derivative represented by the formula (5).

3. A process for producing a sulfonamide derivative represented by formula (6):

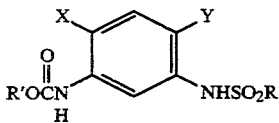
(6)

wherein X and Y independently represent a halogen atom, R represents a C$_1$-C$_4$ alkyl group or a C$_1$-C$_3$ haloalkyl group and R' represents a C$_1$-C$_4$ alkyl group or a phenyl group, comprising the step of halogenating an anilide derivative represented by formula (5):

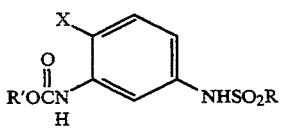
(5)

4. The process of claim 3, wherein the anilide derivative of formula (5):

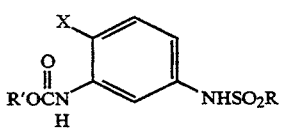
(5)

wherein X represents a halogen atom, R represents a C$_1$-C$_4$ alkyl group or a C$_1$-C$_3$ haloalkyl group and R' represents a C$_1$-C$_4$ alkyl group or a phenyl group, is produced by reacting a diamine derivative represented by formula (2):

(2)

with a halogenoformate represented by formula (12):

Hal—CO$_2$R' (12)

wherein Hal represents a halogen atom.

5. The process of claim 4 wherein the diamine derivative of formula (2):

(2)

wherein X represented a halogen atom and R represents a C$_1$-C$_4$ alkyl group or a C$_1$-C$_3$ haloalkyl group is prepared by reducing a nitroaniline derivative represented by formula (1):

(1)

6. The process of claim 5, wherein the nitroaniline derivative of formula (1):

(1)

wherein X represents a halogen atom and R represents a C$_1$-C$_4$ alkyl group of a C$_1$-C$_3$ haloalkyl group is prepared by reacting 4-halogeno-3-nitroaniline represented by formula (9):

(9)

with an alkylsulfonyl halide represented by formula (11):

Hal—SO$_2$R (11)

wherein Hal represents a halogen atom.

7. The process of claim 3, wherein the anilide derivatives of formula (5):

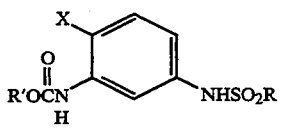
(5)

wherein X represents a halogen atom, R represents a $C_1$–$C_4$ alkyl group of a $C_1$–$C_3$ haloalkyl group and R' represents a $C_1$–$C_4$ alkyl group or a phenyl group is produced by reacting an aminocarbanilide derivative represented by formula (4):

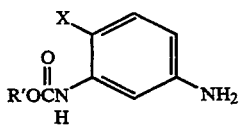
(4)

with an alkylsulfonyl halide represented by formula (11):

(11)

wherein Hal represents a halogen atom.

8. The process of claim 7, wherein the aminocarbanilide derivative represented by formula (4):

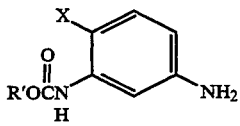
(4)

wherein X represents a halogen atom and R' represents a $C_1$–$C_4$ alkyl group or a phenyl group is produced by reducing a nitrocarbanilide derivative represented by formula (3):

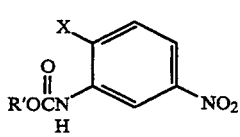
(3)

wherein X is as defined above.

9. The process of claim 8, wherein the nitrocarbanilide derivative represented by formula (3):

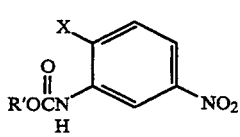
(3)

wherein X represents a halogen atom and R' represents a $C_1$–$C_4$ alkyl group or a phenyl group is produced by reacting 2-halogen-5-nitroaniline represented by formula (10):

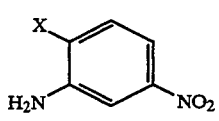
(10)

with a halogenoformate represented by formula (12):

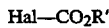
(12)

wherein Hal represents a halogen atom.

* * * * *